United States Patent
Moszner et al.

(10) Patent No.: US 7,932,304 B2
(45) Date of Patent: Apr. 26, 2011

(54) POLYMER-COATED GLASS FILLER FOR USE IN DENTAL MATERIALS

(75) Inventors: Norbert Moszner, Triesen (LI); Jorg Angermann, Sargans (CH); Volker Rheinberger, Vaduz (LI); Dieter Voser, Schaan (LI); Karin Vogel, Gamprin (LI); Simone Klapdohr, Rosenheim (DE)

(73) Assignee: Ivoclar Vivadent AG, Schaan (LI)

( * ) Notice: Subject to any disclaimer, the term of this patent is extended or adjusted under 35 U.S.C. 154(b) by 29 days.

(21) Appl. No.: 12/275,843

(22) Filed: Nov. 21, 2008

(65) Prior Publication Data
US 2009/0239971 A1  Sep. 24, 2009

(30) Foreign Application Priority Data
Mar. 20, 2008  (EP) ..................... 08102842

(51) Int. Cl.
*A61K 6/03* (2006.01)
(52) U.S. Cl. ........ 523/117; 523/115; 523/116; 523/118; 523/119; 523/120
(58) Field of Classification Search ........... 523/115–120
See application file for complete search history.

(56) References Cited

U.S. PATENT DOCUMENTS

| | | | |
|---|---|---|---|
| 3,705,757 A * | 12/1972 | Huber | 359/453 |
| 3,826,778 A | 7/1974 | Dietz | |
| 3,971,753 A * | 7/1976 | Frechtling et al. | 524/789 |
| 4,412,015 A | 10/1983 | Lustgarten et al. | |
| 4,478,961 A * | 10/1984 | Tanaka et al. | 523/105 |
| 5,453,456 A | 9/1995 | Mitra et al. | |
| 6,620,861 B1 | 9/2003 | Nakatuka et al. | |
| 6,797,446 B2 * | 9/2004 | Tamura | 430/78 |
| 6,858,364 B2 * | 2/2005 | Tamura | 430/78 |
| 6,869,984 B2 * | 3/2005 | Kawashima et al. | 523/116 |
| 6,984,673 B2 * | 1/2006 | Kawashima et al. | 523/116 |
| 2008/0081889 A1* | 4/2008 | Kawashima et al. | 526/181 |
| 2010/0087613 A1* | 4/2010 | Takei et al. | 526/313 |

FOREIGN PATENT DOCUMENTS

| | | |
|---|---|---|
| CH | 652 139 A5 | 10/1985 |
| GB | 1 368 061 | 9/1974 |
| WO | 2004/103319 A1 | 12/2004 |

OTHER PUBLICATIONS

Klapdohr and Moszner, "New Inorganic Components for Dental Filling Composites," Monatshefte fur Chemie 136:21-45 (2005).
Moszner and Salz, "Recent Developments of New Components for Dental Adhesives and Composites," Macromol. Mater. Eng. 292:245-271 (2007).
European Search Report dated Aug. 27, 2008.

* cited by examiner

*Primary Examiner* — Peter Szekely
(74) *Attorney, Agent, or Firm* — Ann M. Knab

(57) ABSTRACT

Filler based on glass particles which contain a homo- or copolymer of vinyl chloride on the surface, process for its preparation and its use as a dental material.

25 Claims, 1 Drawing Sheet

POLYMER-COATED GLASS FILLER FOR USE IN DENTAL MATERIALS

This application claims the benefit of European Application No. EP 08102842.5, filed Mar. 20, 2008, which is hereby incorporated by reference in its entirety.

FIELD OF THE INVENTION

The present invention relates to polymer-treated glass fillers which are suitable for use in dental materials, in particular for the preparation of self-adhesive composites.

BACKGROUND OF THE INVENTION

Composites are widely used in restorative dentistry as filling and fixing materials or in orthodontics as cements. Composites are generally defined as a combination of two substances whose properties differ from those of the pure components. In the case of dental composites they are multi-substance systems which consist of an organic monomer or polymer matrix in which one or more fillers are incorporated.

The main function of the fillers in these cases is to improve the mechanical properties of a dental composite, such as e.g. strength, hardness or modulus of elasticity, reduce thermal expansion and polymerization shrinkage and influence the rheological and visual properties of the composites in a targeted way. The dental fillers used for this can be divided into purely organic and inorganic fillers or combinations thereof, wherein inorganic fillers are most often used. These can in turn be divided into oxidic and non-oxidic fillers. The oxidic fillers are then further classified as siliceous and non-siliceous fillers.

The siliceous fillers include ground glasses, such as e.g. barium silicate glasses, strontium silicate glasses, lithium-aluminium-silicate glasses and X-ray-opaque aluminium fluoro-silicate glasses which are used primarily in methacrylate resin-reinforced glass ionomer cements. The siliceous fillers also include pure silicon dioxide fillers which are likewise often used in dental materials. Mixed oxides based on silicon and zirconium oxide or core-shell systems are also known. These are used, alongside the reinforcing action, to increase X-ray opacity and adjust transparency, by adapting the refractive index according to the composition of the filler.

Non-siliceous fillers such as e.g. zirconium oxide, tantalum oxide, ytterbium trifluoride or yttrium oxide are used as X-ray-contrast media. Aluminium and titanium oxide often serve as opacifiers because of their high refractive index.

Dental fillers should as a rule be colourless, resistant in the oral environment and toxicologically acceptable. To improve the mechanical properties, the surfaces of the dental fillers which are e.g. contained in the widely used light-curing composites are functionalized with polymerizable silanes, such as e.g. (meth)acryloyloxyalkyltrialkoxy silanes. The introduced (meth)acrylate groups are then covalently bound to the polymer matrix during the curing of the composites by copolymerization.

Filling composites with self-adhesive properties are currently attracting increased interest (N. Moszner, U. Salz, Macromol. Mater. Eng. 292 (2007) 245-271). These are composites which, alongside the conventional crosslinker or diluting monomers, such as e.g. bis-GMA (2,2-bis[4-(2-hydroxy-3-methacrylo-yl-oxypropoxy)phenyl]propane) or UDMA (1,6-bis[2-methacrylo-yl-oxyethoxycarbony-lamino]-2,4,4-trimethylhexane) or D$_3$MA (deca-ne-di-oldimethacrylate) or TEGDMA (triethylene glycol dimethacrylate), contain strongly acid acid monomers. Such acid monomers, such as e.g. also GDMP (glycerol dimethacrylate dihydrogen phosphate) or MDP (10-methacryloyloxydecyl dihydrogen phosphate) are able to mediate adhesion to dentine and enamel.

If the conventional glass fillers, such as e.g. barium silicate glasses, are used for self-adhesive composites, disadvantageous effects may result. For one thing, the acid monomers of the organic matrix may dissolve cations, e.g. $Ba^{2+}$ ions, out of the particles of the glass fillers. As a result of this, salt may form and, linked to this, there may be a clear viscosity increase of the organic matrix or a perceptible thickening of the composite and thus a deterioration in storage stability. There is also the risk that the acid monomer molecules will become bound to the filler surface because of the reaction of the acid phosphate groups with the filler and are thus no longer available as adhesion promoter for the hard tooth substance.

According to the state of the art the coating of dental glass fillers has already been known for a relatively long time. Thus e.g. EP 0 047 971 B1 or CH 652 139 A5 describe the coating of dental filler particles with a cold-, light- or heat-curable plastic, e.g. based on dimethacrylate.

There are numerous publications on the coating of dental glass powders with homo- or heteropolysiloxanes or sol-gel products, i.e. hydrolytic condensates of different silanes and metal alkoxides, such as Zr, Ti or Al alkoxides or their mixtures (cf. S. Klapdohr, N. Moszner, Monatsh. Chem. 136 (2005) 21-45).

In U.S. Pat. No. 6,620,861 B1, e.g. dental fillers are described in which glass powder particles are coated with polysiloxanes.

The coating of the glass fillers in the aforementioned documents takes place for different reasons and is intended to lead to advantageous properties of the dental materials containing these glass fillers. However, the use of the glass fillers in self-adhesive composites is not described in the above documents, nor is their possible suitability for use in self-adhesive compositions the subject of the disclosed teachings.

U.S. Pat. No. 5,453,456 also relates, not to self-adhesive composites, but to glass ionomer cements and aluminium-fluorosilicate glass fillers contained therein. To improve the mechanical properties of the cured cement while preserving or increasing the desired release of fluoride ions, the aluminium-fluoro-silicate glass filler particles are provided with a coating containing ionic carboxyl groups and siloxy groups. To further improve strength and fracture toughness, the thus-treated aluminium-fluorosilicate glass fillers can optionally be treated with an additional organic compound. Additional organic compounds coming into consideration comprise an extensive list of monomeric, oligomeric and polymeric compounds, wherein unspecifically polymers of different types are named as polymers, e.g. polycondensates, polyadducts and polymerizates, including among others polyvinyl chloride. Preferred additional organic compounds contain ethylenically unsaturated groups and hydrophilic groups, such as, for example, ethylene glycol groups, and in all the embodiment examples in which a treatment with an additional organic compound is carried out, compounds of just this preferred type are preferably used. A coating of the aluminium-fluorosilicate glass filler particles with polyvinyl chloride is not described.

SUMMARY OF THE INVENTION

According to certain aspects, the invention provides glass fillers which in combination with acid organic matrix materials lead, compared with conventional glass fillers, to a clearly increased stability of the paste viscosity (consistency), without disadvantageously influencing the speed of curing of the composites or the mechanical properties of the cured composites. The glass fillers are intended to provide self-adhesive composites whose processing properties are not impaired by storage.

DETAILED DESCRIPTION OF VARIOUS EMBODIMENTS

Figure 1:
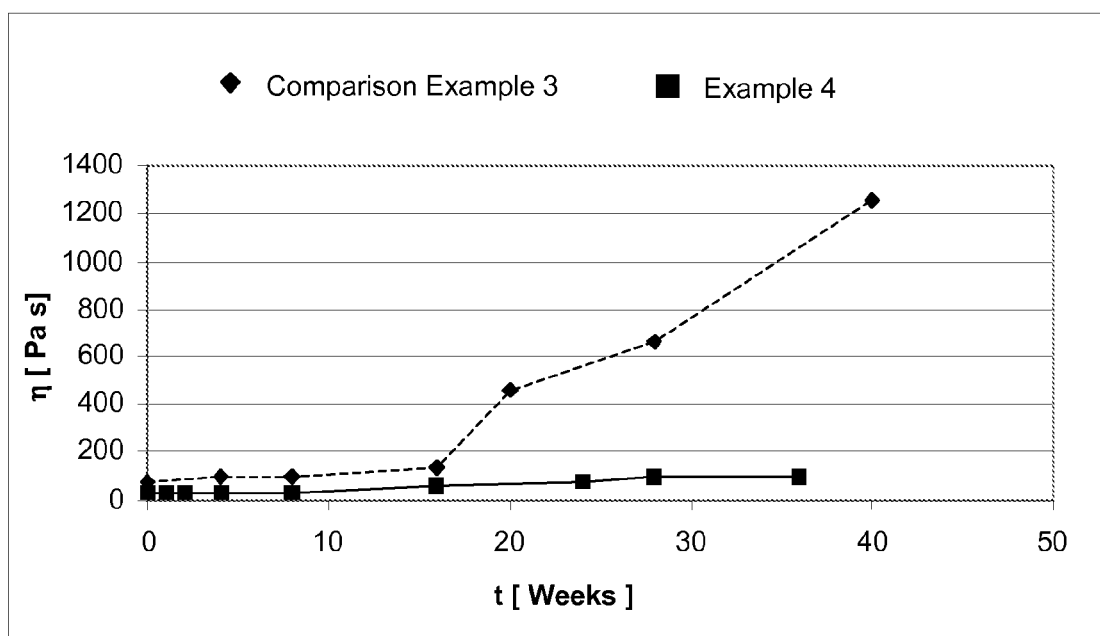
FIG. 1 is a chart measuring viscosity in relation to storage time of composite pastes.

The present invention relates to a filler based on glass particles which is characterized in that the glass particles contain a homo- or copolymer of vinyl chloride on the surface.

The present invention also relates to a dental material which contains this filler, and the use of the filler for the preparation of a dental material.

The subject of the present invention is also a process for the preparation of a filler based on glass particles, in which glass particles are dispersed in a solution of a homo- or copolymer of vinyl chloride in an organic solvent and the solvent is then removed.

The terms "polyvinyl chloride(s)" and "PVC" used in the following cover both homo- and copolymers of vinyl chloride.

The glass particles which form the basis of the filler according to the invention can in principle consist of all glasses which are customarily used in the dental field, including, as a rule, silicate glasses.

The glass particles preferably consist of a glass which contains barium oxide and/or strontium oxide. Glasses which contain 15 to 35 wt.-% barium oxide and/or 15 to 25 wt.-% strontium oxide are particularly preferred.

Glasses which in micronized form display an alkaline reaction when dispersed in water are further preferred. These preferably include glasses which, when 2 g glass particles with a weight-average particle size of approximately 1.5 μm are suspended in 50 ml distilled water (pH=7) by stirring at approx. 20° C., bring about an increase in the pH of the water to at least 8, particularly preferably at least 8.5, after 30 minutes.

In a preferred embodiment the glass used contains little or no fluoride. By this is meant glasses with a fluoride content of 0 to 15 wt.-%, preferably 0 to 10 wt.-%, particularly preferably 0 to 3 wt.-% and quite particularly preferably <1 wt.-%.

In dental materials, an adequate radio opacity is often required in order to allow the material to be distinguished from the natural tooth on an X-ray picture. If the filler according to the invention is provided for use in radio-opaque dental materials, it is therefore advantageous to use a radio-opaque glass. In general, glasses which contain heavy metal ions (mass number >37) show an adequate radio-opacity. Examples of known radio-opaque glasses which are preferably used with the filler of the present invention are barium silicate glass (in particular barium-aluminium-silicate glass) and strontium silicate glass (in particular strontium-aluminium-silicate glass). Preferred compositions of these glasses are 40 to 60 wt.-% $SiO_2$, 10 to 15 wt.-% $Al_2O_3$, 10 to 20 wt.-% $B_2O_3$ and 15 to 35 wt.-% BaO (barium-aluminium-silicate glass) or 40 to 60 wt.-% $SiO_2$, 10 to 15 wt.-% $Al_2O_3$, 10 to 20 wt.-% $B_2O_3$, 0 to 3 wt.-% BaO and 15 to 25 wt.-% SrO (strontium-aluminium silicate glass).

The glass particles used as starting material preferably have an average particle size in the range from 0.01 to 10 μm, particularly preferably from 0.5 to 5 μm and quite particularly preferably 0.6 to 2.0 μm. The average particle size is the weight average, determined by light scattering. It is further advantageous if the glass particles do not contain particles which are larger than 90 μm, preferably larger than 20 μm, i.e. the glass particles can pass through a sieve with the aforementioned mesh widths.

The glass particles preferably have a specific surface—determined using the BET method according to ISO 9277: 1995—of 1 to 30 $m^2/g$, preferably 1 to 20 $m^2/g$ and particularly preferably 3 to 10 $m^2/g$.

Glass particles of suitable sizes can for example be prepared in customary manner by grinding.

To improve the mechanical properties of the cured dental material, it is advantageous to use a filler according to the invention based on a silanized glass. By "silanization" is meant the functionalization of the glass surface with polymerizable silanes, say by reaction with (meth)acrylate-functionalized silanes, e.g. (meth)acryloyloxyalkyl-trialkoxysilanes, usually 3-(methacryloyloxy)propyl-trimethoxy-silane, 3-(methacryloyloxy)propyltriethoxysilane, 3-(methacryloyloxy)-propyltrichlorosilane, methacryloyloxy-methyltrimethoxysilane, methacryloyloxymethyltriethoxysilane, 3-(methacryloyloxy)propylmethyldichlorosilane or 3-(methacryl-oyloxy)propylmethyldimethoxy silane. 3-(Methacryloyloxy)-propyltrimethoxysilane is preferred. The silanization of the glasses takes place in conventional manner and is known to a person skilled in the art.

The glass particles of the filler according to the invention contain a homo- or copolymer of vinyl chloride on the surface. The surface of the glass particles is usually at least partly, preferably for the most part or completely, coated with the polyvinyl chloride.

Polyvinyl chlorides suitable for the fillers according to the invention are for example homo- or copolymers of vinyl chloride customary in the trade, preferably with number-average molecular weights $M_n$ in the range from 30,000 to 130,000, preferably 30,000 to 50,000. In addition to the homopolymers of vinyl chloride that are suitable in particular, preferably with the above-named molecular weights, copolymers of vinyl chloride can also be used. In a preferred embodiment these contain at least 80 mol-% polymerized vinyl chloride units and less than 20 mol-% polymerized units of one or more comonomers. Suitable comonomers are e.g. vinyl acetate, acrylonitrile, ethylene and vinylidene chloride, wherein ethylene and/or acrylonitrile are preferred.

The process by which the PVC was prepared is not decisive for the present invention. Customary preparation processes comprise suspension polymerization, emulsion polymerization and mass polymerization, wherein suspension polymerization is the most important in industrial terms.

To apply the PVC to the glass particles, which can be silanized as described above, the PVC is dissolved in an organic solvent and the glass particles dispersed in this solution.

All organic solvents in which PVC is soluble in an adequate concentration are suitable as solvents. For example, cyclic ketones, say cyclopentanone and cyclohexanone; dimethylformamide; dimethylsulphoxide and in particular tetrahydrofuran (THF) as well as mixtures of these solvents are well suited. The mass content of PVC in the solution is preferably 0.01 to 20 wt.-%, particularly preferably 1 to 7 wt.-%.

The glass particles are dispersed in the PVC solution, preferably accompanied by stirring, then separated from the solution again after an adequate time, usually after a period of 0.2 to 2 h, for example, by centrifuging or filtration, and then dried, e.g. under fine vacuum ($10^2$ to $10^{-1}$ Pa). During drying, it is to be ensured that the temperature lies at least approx. 30° C. below the glass-transition temperature ($T_G$) of the PVC. Thus, in the case of homopolymeric PVC ($T_G$=81° C.) the temperature should not exceed 50° C., in order to prevent the filler particles from agglutinating due to a softened polymer coating.

The quantity of PVC applied to the glass particles can for example be determined by X-ray fluorescence analysis (XRF). The quantity of PVC can be calculated from the quantity of chlorine ascertained by XRF. Typically, the PVC is applied to the glass particles in a quantity such that the weight of the PVC represents 0.1 to 7.0 wt.-%, preferably 1.0 to 5.0 wt.-% of the total weight of the filler particles.

The fillers according to the invention are preferably used for the preparation of dental materials, in particular self-adhesive composites. The composites are particularly suitable as dental tooth-filling materials. In principle the fillers according to the invention can however also be used in other applications, preferably those in which the protection of the glass particles against a surrounding acid environment is of interest.

The subject of the present invention is also a dental material, usually in paste form, which contains the filler according to the invention as described above including its preferred embodiments. The dental material is preferably a self-adhesive composite.

According to a preferred embodiment, the dental material contains:
(a) 1 to 85 wt.-%, in particular 5.0 to 50 wt.-% filler according to the invention as described above including its preferred embodiments,
(b) 0.1 to 5.0 wt.-%, in particular 0.2 to 2.0 wt.-% initiator for the radical polymerization and
(c) 1 to 70 wt.-%, in particular 5.0 to 40 wt.-% of one or more acid group-free radically polymerizable monomers.

Dental materials for use as self-adhesive cements or composites also contain in addition:
(d) 1 to 30 wt.-%, in particular 3.0 to 20 wt.-% of one or more acid group-containing radically polymerizable monomers.

The dental material preferably contains no added solvent. All quoted values are relative in each case to the total weight of the dental material.

Component (b), the initiator for the radical polymerization, is selected depending on whether radiation curing (photochemical radical polymerization), hot curing or curing at room temperature is desired for the dental material according to the invention. By "initiator" is also meant initiator systems of different compounds.

Examples of suitable photoinitiators include benzophenone, benzoin and derivatives thereof and α-diketones and derivatives thereof, such as 9,10-phenanthrenequinone, 1-phenyl-propan-1,2-dione, diacetyl and 4,4-dichlorobenzil. Camphorquinone, 2,2-methoxy-2-phenyl-acetophenone or α-diketones, each in combination with amines as reduction agents, such as e.g. 4-(dimethylamino)-benzoic acid esters, N,N-dimethylaminoethylmethacrylate, N,N-dimethyl-sym.-xylidine or triethanolamine, as well as monobenzoyl- or dibenzoyl germanium derivatives, are preferably used.

Benzopinacol and 2,2'-dialkylbenzopinacols for example are also suitable as initiators for hot curing.

Redox-initiator combinations, such as e.g. combinations of benzoyl peroxide with N,N-dimethyl-sym.-xylidine or N,N-dimethyl-p-toluidine, can be used as initiators for a polymerization carried out at room temperature (cold curing). In addition, redox systems consisting of peroxides and reducing agents, such as e.g. ascorbic acid, barbiturates or sulphinic acids, are also suitable.

Component (c), the acid group-free radically polymerizable monomers, and component (d), the acid group-containing radically polymerizable monomers, jointly represent the binder of the dental material according to the invention which polymerizes radically during curing.

The binder monomers of component (c) comprise so-called crosslinking monomer(s) with at least two, preferably 2 to 4 radically polymerizable groups and so-called diluting monomer(s) whose viscosity and good solubility make them suitable for diluting polymerization resins. Diluting monomers can contain one or also more polymerizable groups and in the latter case also act as crosslinking monomers.

Above all, crosslinking bi- or polyfunctional methacrylates and acrylates are suitable as crosslinking monomers, such as e.g. 1,6-bis[2-methacryloyl-oxyethoxycarbonylamino]-2,4,4-trimethylhexane (UDMA), 2,2-bis[4-(2-hydroxy-3-methacryloyl-oxypropoxy)phenyl]propane (bis-GMA), 1,6-bis[2-acryloyl-oxyethoxycarbonylamino]-2,4,4-trimethylhexane, diethylene glycol dimethacrylate, triethylene glycol dimethacrylate (TEGDMA), diethylene glycol diacrylate, triethylene glycol diacrylate, trimethylolpropane trimethacrylate, trimethylolpropane triacrylate, pentaerythritol tetramethacrylate, pentaerythritol tetraacrylate as well as butanediol dimethacrylate, butanediol diacrylate, 1,10-decanediol dimethacrylate ($D_3MA$), 1,10-decanediol diacrylate, 1,12-dodecanediol dimethacrylate and 1,12-dodecanediol diacrylate, which are accessible by esterification of (meth)acrylic acid with the corresponding di- or polyols. Hydrolysis-resistant crosslinking monomers are also suitable, for example urethanes of 2-(hydroxylmethyl)acrylic acid and diisocyanates, such as 2,2,4-tri-methylhexamethylene diisocyanate and isophorone diisocyanate; crosslinking pyrrolidones, such as e.g. 1,6-bis(3-vinyl-2-pyrrolidonyl)-hexane; commercially accessible bisacrylamides or bis(meth)acrylamides, such as methylene and ethylene bisacrylamide, N,N'-diethyl-1,3-bis(acrylamido)-propane, 1,3-bis(methacrylamido)-propane, 1,4-bis(acrylamido)-butane and 1,4-bis(acryloyl)piperazine which can be synthesized by reaction from the corresponding diamines with (meth)acrylic acid chloride.

The term "hydrolysis-resistant" herein also includes monomers which are stable for at least 6 weeks, i.e. hydrolyse less than 5%, in water or in mixtures of water and water-miscible solvents in a concentration of approx. 20 wt.-% and at a pH approx. 2.0 at 37° C.

Liquid monomers with a viscosity η smaller than 100 mPa·s, measured at 20° C., are preferably used herein as diluting monomers. Examples of diluting monomers include hydrolysis-resistant mono(meth)acrylates, e.g. mesityl methacrylate; 2-(alkoxymethyl)acrylic acids, e.g. 2-(ethoxymethyl)acrylic acid, 2-(hydroxymethyl)acrylic acid; N-mono- or disubstituted acrylamides, such as e.g. N-ethyl acrylamide, N,N-dimethyl acrylamide, N-(2-hydroxyethyl)acrylamide and N-methyl-N-(2-hydroxyethyl)acrylamide or N-monosubstituted methacrylamides, such as e.g. N-ethylmethacrylamide and N-(2-hydroxy-ethyl)methacrylamide. N-vinylpyrrolidone, 2-(methacryl-oyloxy)ethylacetoacetate or allyl ethers can also be used as diluting monomers.

Component (d), the acid group-containing radically polymerizable monomers, is responsible for an improved adhesion of the dental materials to enamel/dentine. These are strongly acid monomers, also called adhesive monomers, which firstly remove a light smear layer on the enamel/dentine when using the dental material and secondly etch the melt or the dentine with the result that monomers can diffuse in and lead, during the following polymerization, accompanied by formation of so-called polymer tags, to a strong bond between the cured dental material and enamel/dentine.

The adhesive monomers (d) preferably contain 1 to 4 acid groups. Preferred acid groups are carboxylic acid, sulphonic acid, phosphonic acid and/or phosphoric acid groups. Compounds which contain carboxylic acid, phosphonic acid and/or phosphoric acid groups as acid groups are particularly preferred. Compounds with more than one acid group can contain different acid groups or preferably identical acid groups. Particularly advantageous adhesive monomers are polymerizable dihydrogen and hydrogen phosphates.

Examples of suitable adhesive monomers (d) include glycerol dimethacrylate dihydrogen phosphate (GDMP), 4-(meth)acryloyl-oxyethyltrimellitic acid anhydride, 10-methacryloyloxy-decylmalonic acid, N-(2-hydroxy-3-meth-acryl-oyloxypropyl)-N-phenylglycine, 4-vinylbenzoic acid, 2-meth-acryloyloxyethyl-phenyl-hydrogen phosphate, 10-methacryloyloxydecyl-dihydrogen phosphate (MDP), 2-methacryloyloxyethyl dihydrogen phosphate and dipentaerythritol pentamethacryloyloxy phosphate. Hydrolysis-resistant adhesive monomers, such as 4-vinylbenzyl phosphonic acid, 2-[4-(dihydroxy-phosphoryl)-2-oxa-butyl]-acryl acid are also advantageous, as well as amides and hydrolysis-resistant esters thereof, such as e.g. 2-[4-(dihydroxyphosphoryl)-2-oxa-butyl]-acrylic acid-2,4,6-trimethylphenylester, as well as (meth)acrylamide dihydrogen phosphates, such as e.g. 6-methacrylamidohexyl- and 1,3-bis(methacrylamido)-propan-2-yl-dihydrogen phosphate.

All the monomers named above by way of example for the individual components can each be used alone or in mixtures.

The dental materials according to the invention preferably contain no polymers or copolymers with acid groups.

The dental materials according to the invention can also contain the fillers according to the invention mixed with one or more other customary fillers (e), such as e.g. inorganic, spherical, amorphous fillers based on oxides, such as $ZrO_2$, $Ta_2O_3$ and $TiO_2$ or mixed oxides of $SiO_2$, $ZrO_2$ and/or $TiO_2$, nanoparticulate or microfine fillers, such as pyrogenic silica, precipitated silica or ytterbium trifluoride, and also so-called "isofillers", i.e. powders which are accessible by grinding cured composites. Preferred weight-average particle sizes of the above-named fillers are in the range from 10 to 200 nm for the oxidic fillers, in the range from 20 nm to 5 µm for the nanoparticulate and microfine fillers and in the range from 5 to 100 µm for the isofillers.

The dental materials according to the invention can optionally contain further additives, e.g. stabilizers, flavourings, colorants, microbiocidal active ingredients, fluoride ion-releasing additives, optical brighteners, plasticizers and/or UV absorbers.

To prepare the dental materials according to the invention, filler (a) according to the invention and the other components (b), (c) and optionally (d) as described above and further filler (e) and additive(s) (f) are mixed.

It was found that the PVC on the surface of the glass particles of the filler according to the invention, when the latter is used in an acid organic matrix, say in a self-adhesive composite, seriously impedes the dissolving out of cations, e.g. $Ba^{2+}$ ions by the acid constituents of the matrix, and thus a salt formation and viscosity increase of the organic matrix is reduced and finally a significant improvement of the storage stability of the pasty dental materials can be achieved. This is surprising, in as much as according to the state of the art the release for example of fluoride ions is not prevented, or is actually improved, by the surface treatment of fillers with polymeric organic compounds.

PVC is practically insoluble in the customary monomers of the matrix, in particular the binder monomers previously called component (c), such as e.g. bis-GMA, UDMA, TEGDMA or $D_3MA$, as well as the strongly acid adhesive monomers of component (d), such as e.g. MDP or GDMP. Thus there is no detachment of the PVC coating during the preparation of the dental materials with a monomer mixture based e.g. on the above-named monomers. Moreover, it was surprisingly shown that the mechanical properties, e.g. the biaxial strength, of the cured dental material are not adversely affected by the PVC coating. It is presumed that the relatively great polarity of PVC is not only advantageous for the film formation on the surface of the glass particles, but apparently also for the filler-matrix bond in the composite. The PVC coating does not reduce the speed of curing of the dental materials, and the dentine adhesion of the dental materials is not adversely affected.

The invention is explained in more detail below by means of examples.

EXAMPLES

Reference Example 1

Silanization of a Glass Filler 93 g glass particles consisting of a barium-aluminium-silicate glass with a weight-average grain size $d_{50}$ of 1.5 µm (Schott A G, Mainz; composition: 55 wt.-% $SiO_2$, 25 wt.-% BaO, 10 wt.-% $B_2O_3$ and 10 wt.-%. $Al_2O_3$) was silanized with addition of 5 g 3-(methacryloyloxy)-propyltrimethoxysilane and 2 g water. The glass filler was introduced first into the Turbular mixer (planetary mixer), followed by the addition of water and mixing. The silane was then added and mixing took place overnight. The glass filler was then screened through a sieve (mesh size 200 µm) and dried for 48 h at 50° C. The glass filler was finally screened through a sieve with a mesh size of 90 µm. After the silanization the organic content corresponding to the loss on ignition was 2.8 wt.-%. A value of 3.9 m²/g was determined for the specific surface of the glass filler, using the customary BET method (ISO 9277:1995). The specific surface was measured by means of $N_2$ absorption with a Quantachrome NOVA 2200e apparatus with 6 measurement points after sample degassing for 18 h at 105° C. under vacuum (<10 mbar). X-ray fluorescence analysis (XRF) detected no chlorine in the glass filler.

Inventive Example 2

Coating of the Silanized Glass Filler with Polyvinyl Chloride 60 g of the silanized glass filler from Reference Example 1 was dispersed in 300 g of 5.0 wt.-% solution of polyvinyl chloride (Aldrich; $M_n$ approx. 35,000) in THF for 30 min and then filtered off. The powder was dried for 5 h on the rotary evaporator at 40° C., agglomerates were split up and sieving was carried out over a screen with a mesh size of 90 µm. The organic content, which was determined via the loss on ignition, is 4.9 wt.-%. The specific surface of the glass filler measured according to BET (determined as described in reference example 1) was 4.0 m²/g. XRF produced a Cl content of 1.3%, which corresponds to a PVC content of 2.3%.

Comparison Example 3 and Inventive Example 4

Preparation and Testing of Composites with the Glass Fillers

A resin matrix was prepared by mixing the following components:

| Quantity | Component |
|---|---|
| 15.0 wt.-% | 10-methacryloyloxydecyl-dihydrogen phosphate (MDP) (adhesive monomer) |
| 3.0 wt.-% | 2-methacryloyloxyethyl-dihydrogen phosphate (adhesive monomer) |
| 66.0 wt.-% | urethane dimethacrylate (UDMA) (crosslinking monomer), |
| 15.0 wt.-% | 2-(methacryloyloxy)-ethylacetoacetate (diluting monomer) |
| 0.3 wt.-% | camphorquinone (initiator), |
| 0.6 wt.-% | 4-(dimethylamino)benzoic acid ethyl ester (initiator) |
| 0.1 wt.-% | additives (stabilizers and UV-absorber) |

Composite pastes of the following composition were prepared with this resin matrix and the glass fillers from Reference Example 1 and Inventive Example 2:

| Component | Comparison Example 3 | Inventive Example 4 |
|---|---|---|
| Resin matrix | 22.8 wt.-% | 22.8 wt.-% |
| Glass filler from Reference Example 1 | 37.1 wt.-% | — |
| Glass filler from Inventive Example 2 | — | 37.1 wt.-% |
| Isofiller* | 37.9 wt.-% | 37.9 wt.-% |
| Bentone ® paste** | 2.2 wt.-% | 2.2 wt.-% |

*Isofiller is a hot-cured composite filler ground to the desired grain size and prepared from: bis-GMA (8.80 wt.-%), UDMA (6.60 wt.-%), 1,10-decanediol dimethacrylate (5.93 wt.-%), dibenzoyl peroxide + 2,6-di-tert-butyl-4-methylphenol (in total 0.67 wt.-%), glass filler, average grain size 0.4 μm (53.0 wt.-%) and $YbF_3$ (25.0 wt.-%)
**Bentone ® 38 (Rheox Inc, Hightown, USA) is an organically modified Mg layered silicate (hectorite) and was introduced into the resin matrix as a 12.5% dispersion.

The monomer mixture was introduced first, then the Bentone® paste and the first half of the quantity of glass filler were added and the composition homogeneously kneaded. The second portion of the quantity of glass filler was then added and kneaded. The first half of isofiller was then added and kneaded, and finally the remaining isofiller added and the paste homogeneously kneaded. Finally, the paste was vented for 15 min at 20,000 Pa.

The viscosity of the composite pastes was measured in relation to the storage time of the pastes at 50° C. with the help of a Bohlin CVO-10 rheometer (Bohlin, Pforzheim) at a shear rate of 1 s$^{-1}$ at 23° C. The influence of the glass filler treatment on the viscosity η in relation to time t is shown in FIG. 1.

The results demonstrate a clear improvement in the storage stability of the composite paste according to the invention.

Testpiece disks (height: 1.2 mm, diameter: 15 mm) were prepared from the composite pastes according to EN ISO 6872: 1998 in steel moulds which were insulated with a 3% V-wax solution in hexane over an irradiation time of 2 times 3 min on both sides with a Spectramat® (Ivoclar Vivadent A G, Liechtenstein) and the biaxial strength of the testpieces after 24 h storage in water at 37° C. was measured:

| Comparison Example 3: | 115.6 ± 9.4 MPa, |
|---|---|
| Inventive Example 4: | 117.1 ± 14.7 MPa. |

The comparison of the two composites shows that the PVC coating does not lead to a disadvantageous influencing of the mechanical properties.

Although various embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

The invention claimed is:
1. A light-curing dental material comprising
 (a) 1 to 85 wt.-% filler based on glass particles, comprising glass particles the surface of which is at least partially coated with a homo- or copolymer of vinyl chloride;
 (b) 0.1 to 5.0 wt.-% photoinitiator for the radical polymerization; and
 (c) 1 to 70 wt.-% of one or more acid group-free radically polymerizable monomers, in each case relative to the total weight of the dental material.
2. The dental material according to claim 1, in which the homo- or copolymer of vinyl chloride has a number-average molecular weight $M_n$ in the range from 30,000 to 130,000.
3. The dental material according to claim 1, in which the glass is a silicate glass.
4. The dental material according to claim 1, in which the glass contains at least one selected from the group consisting of barium oxide and strontium oxide.
5. The dental material according to claim 4, in which the glass contains at least one of 15 to 35 wt.-% barium oxide and 15 to 25 wt.-% strontium oxide.
6. The dental material according to claim 1, further comprising the glass in micronized form which displays an alkaline reaction when dispersed in water.
7. The dental material according to claim 1, in which the glass has a fluoride content of <1 wt.-%.
8. The dental material according to claim 1, in which the glass is X-ray opaque.
9. The dental material according to claim 3, in which the glass is barium silicate glass or strontium silicate glass.
10. The dental material according to claim 9, in which the glass contains 40 to 60 wt.-% $SiO_2$, 10 to 15 wt.-% $Al_2O_3$, 10 to 20 wt.-% $B_2O_3$ and 15 to 35 wt.-% BaO.
11. The dental material according to claim 9, in which the glass contains 40 to 60 wt.-% $SiO_2$, 10 to 15 wt.-% $Al_2O_3$, 10 to 20 wt.-% $B_2O_3$, 0 to 3 wt.-% BaO and 15 to 25 wt.-% SrO.
12. The dental material according to claim 1, in which the glass is silanized.
13. The dental material according to claim 1, in which the surface of the glass particles is at least partially coated with polyvinyl chloride or a copolymer of vinyl chloride, which contains at least 80 mol-% polymerized vinyl chloride units and up to 20 mol-% polymerized units of one or more comonomers.
14. The dental material according to claim 1, in which the glass particles measured without the surface homo- or copolymer of vinyl chloride have an average particle size in the range from 0.01 to 10 μm.
15. The dental material according to claim 1, in which the glass particles have a specific surface—determined using the BET method according to ISO 9277:1995—of 1 to 30 m$^2$/g.

16. The dental material according to claim 1, which further comprises
(d) 1 to 30 wt.-% of one or more acid group-containing radically polymerizable monomers.

17. The dental material according to claim 16, wherein the dental material is a self-adhesive composite which substantially maintains viscosity for a period of about 20 weeks.

18. The dental material according to claim 1, wherein the photoinitiator is selected from the group consisting of benzophenone, benzoin and α-diketones.

19. The dental material according to claim 1, wherein the photoinitiator is selected from the group consisting of camphorquinone, 2,2-methoxy-2-phenyl-acetophenone and α-diketones, each in combination with amine as reduction agent.

20. The dental material according to claim 19, wherein the amine is selected from the group consisting of 4-(dimethylamino)-benzoic acid esters, N,N-dimethylaminoethylmethacrylate, N,N-dimethyl-sym.-xylidine and triethanolamine.

21. The dental material according to claim 1, wherein the one or more acid group-free radically polymerizable monomers comprise monomers with at least two radically polymerizable groups.

22. The dental material according to claim 21, wherein the monomers with at least two radically polymerizable groups are selected from the group consisting of bi- and polyfunctional methacrylates and acrylates.

23. The dental material according to claim 1, wherein the dental material is a single-component composite.

24. The dental material according to claim 16, wherein the dental material is a single-component self-adhesive composite.

25. The dental material according to claim 24, wherein the dental material is a single-component self-adhesive composite which substantially maintains viscosity for a period of about 20 weeks.

* * * * *